(12) United States Patent  
Gill

(10) Patent No.: US 9,132,265 B2  
(45) Date of Patent: Sep. 15, 2015

(54) METHOD AND APPARATUS FOR FLUID DELIVERY

(71) Applicant: RENISHAW (IRELAND) LIMITED, Swords (IE)

(72) Inventor: Steven Streatfield Gill, Bristol (GB)

(73) Assignee: RENISHAW (IRELAND) LIMITED, Swords (IE)

( * ) Notice: Subject to any disclaimer, the term of this patent is extended or adjusted under 35 U.S.C. 154(b) by 0 days.

(21) Appl. No.: 14/262,159

(22) Filed: Apr. 25, 2014

(65) Prior Publication Data

US 2014/0236128 A1 Aug. 21, 2014

Related U.S. Application Data

(63) Continuation of application No. 12/224,655, filed as application No. PCT/GB2007/000850 on Mar. 12, 2007, now Pat. No. 8,747,371.

(30) Foreign Application Priority Data

Mar. 13, 2006 (GB) .................................. 0604929.0

(51) Int. Cl.
*A61M 25/16* (2006.01)
*A61M 39/02* (2006.01)
(Continued)

(52) U.S. Cl.
CPC ............. *A61M 39/0208* (2013.01); *A61M 5/14* (2013.01); *A61M 39/0247* (2013.01);
(Continued)

(58) Field of Classification Search
CPC ............. A61M 2039/0264; A61M 2210/0693; A61M 2210/06; A61M 2210/1021; A61M 39/105; A61M 5/14276; A61M 5/14244; A61M 39/0247; A61M 2039/025; A61M 5/1408

USPC ......... 604/535, 891.1, 890.1, 288.01, 288.02, 604/288.03, 288.04, 151, 175, 174, 258, 604/523, 513

See application file for complete search history.

(56) References Cited

U.S. PATENT DOCUMENTS 3,752,162 A 8/1973 Newash
4,367,740 A 1/1983 Evanoski, III
(Continued)

FOREIGN PATENT DOCUMENTS

WO WO 03/077758 A1 9/2003
WO WO 2007/104961 A1 9/2007

OTHER PUBLICATIONS

Jan. 8, 2015 Office Action issued in European Application No. 07 731 998.6.

(Continued)

*Primary Examiner* — Bhisma Mehta
*Assistant Examiner* — Hamza Darb
(74) *Attorney, Agent, or Firm* — Oliff PLC

(57) ABSTRACT

A method for delivering fluid to a brain of a subject using a modular fluid delivery apparatus is described. The method comprises taking a subject having a first part of the modular fluid delivery apparatus subcutaneously implanted therein, the first part of the modular fluid delivery apparatus comprising a first end having a first fluid connector portion attached thereto and a second end being connected to one or more catheters implanted within the brain of the subject. The method also comprises taking a second part of the modular fluid delivery apparatus, the second part comprising a third end comprising a second fluid connector portion. The method further comprises making an incision in the subject to gain access to the first fluid connector portion of the first part of the modular fluid delivery apparatus, and connecting the first fluid connector portion to the second fluid connector portion.

20 Claims, 6 Drawing Sheets

(51) Int. Cl.
*A61M 39/10* (2006.01)
*A61M 5/14* (2006.01)
*A61M 5/142* (2006.01)

(52) U.S. Cl.
CPC ............ *A61M 39/10* (2013.01); *A61M 5/1408* (2013.01); *A61M 5/14244* (2013.01); *A61M 2039/025* (2013.01); *A61M 2039/0205* (2013.01); *A61M 2039/1066* (2013.01); *A61M 2205/04* (2013.01); *A61M 2210/0693* (2013.01)

(56) References Cited

U.S. PATENT DOCUMENTS

| | | |
|---|---|---|
| 4,479,798 A | 10/1984 | Parks |
| 4,548,607 A | 10/1985 | Harris |
| 4,695,273 A | 9/1987 | Brown |
| 4,701,159 A | 10/1987 | Brown et al. |
| 4,950,255 A | 8/1990 | Brown et al. |
| 5,411,490 A | 5/1995 | Tennican et al. |
| 5,632,729 A | 5/1997 | Cai et al. |
| 5,782,645 A | 7/1998 | Stobie et al. |
| 6,945,969 B1 | 9/2005 | Morris et al. |
| 7,722,580 B2 | 5/2010 | Dicarlo et al. |
| 2002/0156462 A1* | 10/2002 | Stultz .................. 604/891.1 |
| 2003/0004520 A1 | 1/2003 | Haarala et al. |
| 2003/0216714 A1 | 11/2003 | Gill |
| 2004/0215173 A1* | 10/2004 | Kunst .................. 604/891.1 |
| 2004/0249361 A1 | 12/2004 | Denoth et al. |
| 2005/0273083 A1 | 12/2005 | Lebel et al. |
| 2005/0283203 A1 | 12/2005 | Flaherty et al. |
| 2006/0106361 A1* | 5/2006 | Muni et al. .................. 604/500 |

OTHER PUBLICATIONS

U.S. Appl. No. 12/224,653, filed Sep. 3, 2008 in the name of Steven Streatfield Gill.
May 8, 2013 Office Action issued in European Patent Application No. 07 731 998.6.

* cited by examiner

| Condition | Type of Agent | Examples | Number of Catheters | Infusion Rate (μl/min) | Required Volume | Pulsed Delivery | Duration of Treatment |
|---|---|---|---|---|---|---|---|
| Parkinson Disease | Growth Factors | GDNF | 2 | 0.5-5 | Striatum | Y | Long-term |
| | Viral Vectors | GDNF Gene | 2 | 0.5-5 | Striatum | N | Short-term |
| | Liposomes | GDNF Gene | 2 | 0.5-5 | Striatum | N | Short-term |
| | Antisense Oligonucleotides | Anti-Parkin Gene | 2 | 0.5-5 | Striatum | N | Long-term |
| | RNA Interference | Anti-Parkin Gene | 2 | 0.5-5 | Striatum | Y | Long-term |
| Alzheimers Disease | Growth Factors | NGF | 4-7 | 5-10 | Nucleus Basalis | Y | Long-term |
| | Viral Vectors | NGF Gene | 4-7 | 5-10 | Nucleus Basalis | N | Short-term |
| | Liposomes | NGF Gene | 4-7 | 5-10 | Nucleus Basalis | N | Short-term |
| Huntingtons Disease | Growth Factors | CNTF | 4-7 | 5-10 | Cerebral Hemispheres | Y | Long-term |
| | Viral Vectors | CNTF Gene | 4-7 | 5-10 | Cerebral Hemispheres | N | Short-term |
| | Liposomes | CNTF Gene | 4-7 | 5-10 | Cerebral Hemispheres | N | Short-term |
| | Antisense Oligonucleotides | Anti-Huntingtin Gene | 4-7 | 5-10 | Cerebral Hemispheres | Y | Long-term |
| | RNA Interference | Anti-Huntingtin Gene | 4-7 | 5-10 | Cerebral Hemispheres | Y | Long-term |
| Spinocerebellar Ataxia | RNA Interference | Anti-SCA Gene | 3-5 | 0.5-5 | Basal Ganglia, Pons, Cerebellum | Y | Long-term |
| | Antisense Oligonucleotides | Anti-SCA Gene | 3-5 | 0.5-5 | Basal Ganglia, Pons, Cerebellum | Y | Long-term |
| Primary and Secondary Tumours | Novel Chemotherapeutics | Tricyclics | 6-8 | 5-10 | Variable | Y | Short-term |
| | Conventional Chemotherapeutics | Nitrosureas | 6-8 | 5-10 | Variable | Y | Short-term |
| | Immunotoxins | Transferrin-Diphtheria Toxin Constructs | 6-8 | 5-10 | Variable | Y | Short-term |
| | Viruses | Oncolytic HSV | 6-8 | 5-10 | Variable | Y | Short-term |
| | Monoclonal Antibodies | CD44 Antibody | 6-8 | 5-10 | Variable | Y | Short-term |
| Friedreich's Ataxia | Anti-Oxidants | Idabenone | 1-8 | N/K | Variable | Y | Long-term |
| Multiple Sclerosis | Immunomodulators | Interferon | 1-8 | 0.5-10 | Plaque | Y | Long-term |
| | Viral Vectors | Interferon Gene | 1-8 | 0.5-10 | Plaque | N | Short-term |
| | Liposomes | Interferon Gene | 1-8 | 0.5-10 | Plaque | N | Short-term |
| Vasospasm | Growth Factors | MGF | 4-8 | 5-10 | Cerebral Hemispsheres | Y | Short-term |

Fig. 14

METHOD AND APPARATUS FOR FLUID DELIVERY

This is a Continuation of application Ser. No. 12/224,655 filed Sep. 3, 2008, which is a a National Stage of Application No. PCT/GB2007/000850 filed Mar. 12, 2007. The prior application, including the specification, drawings and abstract are incorporated herein by reference in their entirety.

The present invention relates to apparatus for delivering fluids, such as drugs, to different parts of the human or animal body. In particular, the invention relates to modular drug distribution apparatus for delivering drugs to the brain.

The drug treatment of a number of neuro-degenerative disorders, hereditary neurological disorders, brain tumours and other diseases of the nervous system are compromised by the presence of the blood brain barrier which prevents the transfer of drugs from the vascular system or cerebrospinal fluid into the brain substance. Examples of drugs which do not adequately cross the blood brain barrier include protein molecules such as neurotrophins, monoclonal antibodies, viral particles for delivery of gene therapy, as well as a number of cytotoxic drugs for the treatment of tumours.

Such drugs may be delivered to the brain by direct infusion into the parenchyma via an indwelling catheter. Upon exiting the catheter the drugs will be dispersed through the brain substance down a concentration gradient (i.e. by diffusion) and/or down a pressure gradient by the process of convection. Large molecules diffuse poorly and so drug delivery into the brain may be best modulated by controlling the rate of drug infusion and thus the degree to which the drug is convected. Convected infusate will carry large molecules such as proteins and viral particles by bulk flow through the interstitial spaces to fill the selected brain volume.

For a number of conditions it is desirable to maximise the volume of drug delivery from a single catheter, as well as to achieve a homogenous concentration of drug throughout the treatment volume. The process by which this is achieved is termed convection enhanced delivery. This may be accomplished, by inserting a catheter with a small external diameter. For example, a catheter of the type described in WO2003/077785 could be used. The drug can then be infused at a flow rate which will preferentially drive the infusate into the interstitial fluid at a maximum tolerated rate that will not cause tissue damage, but also at a rate which will prevent significant reflux along the catheter tissue interface.

For a number of neurological conditions it is desirable to deliver drugs to large volumes of the central nervous system and these would include the treatment of primary or secondary brain tumours, hereditary disorders and conditions such as multiple sclerosis, where any part of the central nervous system may be affected. In these circumstances, it is often desirable to implant multiple catheters into the central nervous system in order to fill the desired volume of tissue with drug. In other conditions it may be desirable to confine a drug to a particular tissue volume so as to minimise its side effects; for example the delivery of Glial derived neurotrophic factor ("GDNF") to the striatum to promote its reinnervation with dopaminergic neurons. In these circumstances the desired treatment volume may be filled with a single catheter and the flow rate adjusted to fill the desired volume only.

A variety of implantable drug delivery systems are known and typically comprise a drug pump assembly that can be implanted into the abdomen and one or more flexible catheters that route drug from the pump to the required anatomical site or sites. An example of such an implantable pump is described in US2003/0216714.

For some applications, however, it is not desirable to implant a pump for drug delivery because infrequent repeated treatments are required, such as every few months, which would negate the necessity for long-term implantation of a pump. Additionally for treatments requiring drug delivery to a substantial portion of the central nervous system large volumes of infusate may be required, for example in excess of 50 ml, which would require an excessively large pump reservoir to be implanted which would be inappropriate for infrequent use. Furthermore, some drugs may be unstable when stored at body temperature thus preventing the long term storage of such drugs within implanted reservoirs.

In order to be able to deliver drugs intermittently to the brain using an external pump assembly, the clinician is faced with several problems. The most significant problem is the risk of infection at the site where the tubing connecting the intraparenchymal catheter to the pump exits the skin. Although it is known that tubing for drug delivery into the venous system can be implanted for several months and remain substantially infection free with meticulous aseptic technique, an example of which is the Hickman line, this solution would not be suitable for intermittent drug delivery to the brain because the consequences of infection would be far greater and the period over which intermittent therapy may be given could extend over several years.

An alternative drug delivery solution may be to pass a needle through the skin to a subcutaneous drug infusion port, however, although the skin could be cleaned it cannot be made sterile and there remains a not insignificant risk of the needle carrying bacteria into the subcutaneous infusion port. If the infusion period is continued over many hours or a few days then the risk of infection along the needle track significantly increases. A sharp needle can also carry with it skin debris and this may be carried into the brain, or alternatively block the very fine tubing used for convection enhanced delivery. Furthermore, infusion pressures for convection enhanced delivery may be relatively high because of the very fine bore catheter tubing and extension tubing required. Retaining a transcutaneous needle in an infusion port would in these circumstances also be a concern. Additionally where drug delivery is required to multiple sites within the central nervous system, for example six or more, these problems are similarly multiplied.

According to a first aspect of the present invention, fluid delivery apparatus comprises; a first length of implantable tubing having a first end; a first fluid connector portion attached to the first end of the first length of implantable tubing, the first fluid connector portion being releaseably connectable to a complementary second fluid connector portion; and an implantable housing for enclosing the first fluid connector portion, wherein the implantable housing is openable to provide access to the first fluid connector portion.

Apparatus of the present invention thus comprises a first length of tubing having a first end that terminates at a first fluid connector portion which is enclosed within an implantable housing. The first length of tubing, the first fluid connector portion and the implantable housing are hereinafter collectively termed the first part of the (modular) fluid delivery apparatus. Following an initial surgical procedure to implant the first part of the modular apparatus, that first part is fully contained within the body and thereafter should not act as a source of infection. Such an initial surgical procedure may be relatively complex. For example, the first part may also include catheters or the like that are located at certain regions within the body (e.g. within the brain) using high precision techniques. After implantation, the first part of the fluid delivery apparatus may remain inside the body for prolonged periods of time (e.g. months or years), with the implantable housing performing the function of ensuring the fluid connector portion does not become clogged, blocked or damaged by the formation of fibrous tissue. During periods in which fluid delivery is required, a simple surgical procedure may be performed in which an incision is made to uncover the implantable housing. The first fluid connector portion may then be accessed by opening the implantable housing.

As described in more detail below, the apparatus may further comprise a second length of tubing having a first end to which a second fluid connector portion is attached. The second fluid connector portion may be releaseably connectable to the first fluid connector portion thereby allowing fluid communication to be established between the lumen(s) of the first length of tubing and the second length of tubing. The second length of tubing and the second fluid connector portion are hereinafter collectively termed the second part of the (modular) fluid delivery apparatus. An external pump assembly may also be connected to the second end of the second length of tubing. The second part of the modular fluid delivery apparatus is preferably connected to the first part for relatively short periods of time (e.g. hours or days) only when fluid delivery is required. For example, drug delivery may be required for a period of a few hours or days every month or so. Whilst the second part is connected to the first part, the second length of tubing may pass through an incision in the skin.

Although a surgical procedure is typically required to access the implantable housing after implantation of the first part, such a procedure would be of greatly reduced complexity compared with implantation of the first part and simply involves accessing the implantable housing to make the necessary fluid connection between the first and second parts of the modular apparatus. During periods when no delivery of fluid is required, the second part can be removed; the incision through the skin can then be left to heal and there will be no tubes or connectors exiting the skin which can introduce infection into the body. The present invention can thus be seen to be advantageous over Hickman lines and the like where meticulous cleaning of tubes passing through the skin is required for prolonged periods of time (even if no drug delivery is actually required for extended periods). Providing apparatus of the present invention thus overcomes a number of the problems that are traditionally associated with using external pump assemblies.

The apparatus of the present invention also has a number of advantages over fully implantable pump systems of the type described above. For example, implanted pumps have a finite reservoir capacity making them unsuitable for delivering large quantities of fluid. Although implanted reservoirs can be refilled percutaneously, such a refilling process may introduce foreign matter (e.g. skin particles and/or bacteria) into the fluid that is delivered. In contrast, external pumps can be kept completely sterile and may comprise large reservoirs that can be filled quickly. The use of an external pump assembly also permits drugs to be dispensed that have a short half life or which must be stored in certain conditions (e.g. at a low temperature) prior to use. It should also be noted that providing an implantable housing (as opposed to implanting a length of tubing terminated at a connector) allows a surgeon to make a incision to access the first fluid connector portion contained within the housing with a reduced chance of damaging the connector portion or the first length of tubing in the process.

Advantageously, the implantable housing defines a cavity for enclosing a coil of said first length of tubing. Providing a cavity for enclosing a coil of tubing ensures that movement of the subject is not restricted. As the subject moves, any tension in the first length of tubing will be released by unwinding or tightening of the coil. Providing the coil within the housing prevents tissue growth through the coil which might, over time, reduce the amount of coil movement that is possible. The implantable housing may also comprise a fluid sealed aperture through which the first length of tubing is passed from the inside to the outside of the implantable housing.

The openable implantable housing may be formed from a suitable resilient material, such as stainless steel, titanium, plastic etc. Conveniently, the implantable housing protects the first fluid connector portion when closed. For example, the implantable housing may enclose the first fluid connector portion in a cavity that is sealed to the external environment. Conveniently, the implantable housing comprises a body portion having an opening through which the first fluid connector portion can be accessed. A cover for closing the opening in the implantable housing may also be provided; such a cover may be attached to the body portion by a hinge or screw thread. In a preferred embodiment, the housing comprises a lid, which may be secured to a base or body portion using screws or the like, to allow access to the first fluid connector portion that is contained therein. It should be noted that such an implantable housing defining a cavity for enclosing a coil of tubing or cable may be used in other applications. In other words, an implantable housing may be provided that defines a cavity for enclosing a coil of tubing or cable.

Advantageously, a sealing member is provided to prevent fluid egress from the first end of the first length of tubing when the first fluid connector portion is unattached to a complimentary second fluid connector portion. In other words, the first fluid connector portion is arranged such that, in the absence of an attached complimentary connector portion, fluid egress from the first end of the first length of tubing is prevented. The first fluid connector portion may thus be a self sealing or automatic stop connector portion; e.g. it may comprise a septum seal. A cap may be provided for sealing the first fluid connector portion when it is not attached to a complimentary second fluid connector portion; the cap may form part of the implantable housing or be enclosed within that housing. Conveniently, the first fluid connector portion is arranged to provide a substantially sterile fluidic connection with an attached complimentary connector portion.

Advantageously, the implantable housing is configured for subcutaneous implantation within the torso. For example, the implantable housing may have means by which it can be attached to the subcutaneous tissues. Any location where the housing is implanted is preferably easily accessible.

Preferably, the first length of tubing comprises a bundle of one or more single lumen tubes encased in a protective sheath. Alternatively, one or more lumens may be formed in a single piece of material which may also act as the sheath. In either case, the sheath may be reinforced; for example, it may comprise a toughened coating. A length of tubing may also be provided having an inner multi-lumen bundle (e.g. a plurality of separate tubes or a multi-lumen tube) that is slideable within an outer protective sheath. The inner multi-lumen bundle may then be inserted into, and withdrawn from, the outer sheath even after the outer sheath has been implanted in the body. This would allow the inner multi-lumen bundle to be easily replaced (e.g. if a lumen became blocked or started leaking) without having to remove the outer sheath; the complexity of surgical intervention required would thus be reduced. Preferably, the first length of tubing is flexible.

Advantageously, the first length of tubing comprises N lumens, wherein N equals at least two. In other words, the first length of tubing may have multiple internal cores or lumens for carrying fluid. In this manner, separate fluid pathways may be provided from the first fluidic connector portion to the second end of the first length of tubing.

Conveniently, a first fluid router may be attached to the second end of the first length of tubing, the first fluid router being arranged to establish fluid communication between each of the N lumens of the first length of tubing and N output ports. Advantageously, N catheters may also be provided wherein each catheter is in fluid communication with an output port of the first fluid router. The first fluid router may thus provide a means of fanning out fluid connections from the various lumens to separate catheters. Preferably, each catheter is suitable for delivery of fluid to the central nervous system. For example, the catheters may be designed for implantation within the brain. The distal ends of such catheters may be precisely located within the brain as required. In such a case, the first fluid router may be skull mountable; for example, the first fluid router may comprise flanges or protrusions that allow it to be attached to the skull using screws or sutures. Lengths of single lumen tubing may be run from the fluid router to the catheters.

The first fluid connector portion may take a number of forms. For example, the first fluid connector portion may comprise a comprise a plurality of separate connectors (e.g. one per lumen) that can be connected to complimentary connectors of the second part of the modular apparatus. Each of these connectors may be encased in the housing. The first fluid connector advantageously comprises a single connector that provides a plurality of fluid connections. Advantageously, the first fluid connector portion comprises a plurality of chambers, each chamber comprising a resilient (re-sealable) membrane or septum seal through which a hollow needle can be passed. Preferred features of such a female connector portion, and the associated complimentary male connector portion, are outlined in more detail below.

As mentioned above, the apparatus may also comprise a second length of tubing having a first end and a second fluid connector portion attached to the first end of the second length of tubing, wherein the second fluid connector portion is releaseably connectable to the first fluid connector portion. This second part of the modular apparatus may be connected to the first part whenever fluid delivery is required.

Advantageously, the second length of tubing comprises a bundle of one or more single lumen tubes encased in a protective sheath. The second length of tubing may comprises M lumens, wherein M equals at least two. In other words, a multi-core tube may be provided. The second length of tubing may be of similar construction to the first length of tubing that is described above. The number of lumens in the first length of tubing of the first part may be the same as the number of lumens in the second length of tubing of the second part; i.e. N may equal M. However, N may differ from M if required.

Advantageously, the second fluid connector portion comprises a plurality of hollow needles. Preferred features of such a male connector portion, and details of the associated complimentary female connector portion, are outlined below.

Preferably, a second fluid router is attached to the second end of the second length of tubing, the second fluid router being arranged to establish fluid communication between each of the M lumens of the second length of tubing and M input ports. The second fluid router may be arranged to be located externally to the body and acts to fan out the input tubes to allow easy attachment to an associated (external) pump assembly.

Advantageously, the apparatus comprises an external pump assembly for pumping fluid into any one or more of the M input ports of the second fluid router. The pump assembly may be arranged to have control over the pressure and/or flow rate of fluid passed to each input port. The pump assembly may be configured to route fluid to each input port in turn, or it may provide for simultaneous delivery. It should also be noted that the pump may contain the second fluid router. It can thus be seen that, when the modular fluid delivery apparatus is assembled, the external pump provides control over the pressure and/or flow rate of the fluid that is pumped to each of the catheter(s).

All or selected parts of the apparatus of the present invention may be supplied as a kit of parts. In particular, the first and second parts described above may be supplied as a single kit. The present invention also encompasses providing the first and second parts of the apparatus as separate items. A first part of modular fluid delivery apparatus may be thus be provided, the first part being suitable for implantation within the body and comprising a first length of tubing having a first end and a second end, the first end having a first fluid connector portion attached thereto, wherein the first part further comprises an implantable housing for enclosing the first fluid connector portion. A second part of modular fluid delivery apparatus may also be separately provided, the second part comprising a second length of tubing having a first end and second end, wherein the first end of the second length of tubing comprises a second fluid connector portion, the second fluid connector portion being connectable to a first fluid connector portion of an above described first part. The first fluid connector portion of the first part may, during use, be connected to the second fluid connector portion of the second part. The second part (or components thereof) may be disposable (e.g. used to connect to the first part once and then disposed of) or re-useable (e.g. connected to the first part each time fluid delivery is required).

According to a second aspect of the invention, implantable apparatus comprises tubing having a first end and a second end, the first end having a fluid connector portion attached thereto and the second end being connected to one or more catheters for delivering fluid to the brain of a subject, wherein the fluid connector portion is arranged to receive fluid from an external pump assembly and said tubing is sufficiently long to enable said fluid connector portion to be implanted in the torso of the subject.

In this manner, a tube may be passed to the outside of the body in a location that is remote to the central nervous system and so reduces the chance of infection reaching it. The tubing may comprise a plurality of lumens and a plurality of associated catheters may be provided.

According to a third aspect of the invention, a method of drug delivery comprises the steps of; (i) taking a subject (e.g. an animal or human body) having the first part of modular fluid delivery apparatus implanted therein, the first part of the modular fluid delivery apparatus comprising a first length of tubing having a first end and a second end, the first end having a first fluid connector portion attached thereto and the second end being connected to one or more catheters implanted so as to deliver fluid to one or more anatomical sites within the subject, (ii) taking the second part of a modular fluid delivery apparatus, the second part comprising a second length of tubing having a third end comprising a second fluid connector portion, making an incision in the subject to gain access to the first fluid connector portion of the first part of the modular fluid delivery apparatus, and connecting said first fluid connector portion to said second fluid connector portion.

As would be appreciated by a person of ordinary skill, step (ii) requires only a simple surgical procedure that involves making a small incision to provide access to the first fluid connector portion. Step (i) may comprise implanting the first part of the modular fluid delivery apparatus in a subject and may conveniently comprise the step of implanting a plurality of catheters in the brain of the subject. This is a much more involved and complex surgical procedure in which catheters may need to be positioned with a high degree of accuracy.

Advantageously, the method comprises the step (iii) of pumping fluid to said one or more implanted catheters through said first and second parts of the modular fluid delivery apparatus. The fluid may be a drug; for example, a drug of the type described in more detail below with reference to FIG. 14.

Advantageously, the method comprises the further step (iv) of disconnecting the first fluid connector portion from the second fluid connector portion and completely withdrawing the second part of the modular fluid delivery apparatus from the subject. Again, this is a relatively straightforward surgical procedure. Advantageously, steps (ii) to (iv) are repeated in sequence a plurality of times. For example, these steps may be repeated each time delivery of drug is required.

Connector portions suitable for inclusion in apparatus of the present invention are described in co-pending patent application GB0604952.2, the contents of which are hereby incorporated by reference. In particular, and as outlined above, a male fluid connector portion may be provided which comprises a plurality of hollow needles. In a preferred embodiment, there is provided a male fluid connector portion for tubing having a plurality of lumens, the male fluid connector portion being releaseably connectable to a complimentary female fluid connector portion, the male fluid connector portion comprising; a plurality of hollow needles, the hollow needles being arranged such that, when tubing having a plurality of lumens is coupled to the male fluid connector portion, each hollow needle is in fluid communication with one lumen of the tubing; and an alignment guide that allows the hollow needles to be uniquely aligned with the corresponding septum seals of an associated complimentary female fluid connector portion.

Each hollow needle comprises an elongate tube defining a passageway or central channel through which fluid may pass. Each hollow needle may have a proximal end via which it is connected to a fluid supply tube and a distal end (or tip) that may be shaped (e.g. tapered or sheared to a sharp point) to allow it to penetrate the membrane of an associated female connector portion. An aperture may be provided at the tip of the needle and/or on the side of the needle near the tip.

Providing a plurality of needles permits a plurality of separate fluid connections to be made with a complimentary female connector portion. Such a multi-lumen connector enables lengths of multi-lumen tubing to be quickly connected and/or disconnected as required. Such a male fluid connector portion also permits sterile connections to be made and is typically more compact than an arrangement which uses a plurality of single connector portions. A male fluid connector portion of this type is particularly suited for use in the modular fluid delivery apparatus described above, but may also be used in a variety of different medical applications.

Advantageously, the male fluid connector portion comprises an alignment guide to provide alignment of said male fluid connector portion with a complimentary female fluid connector portion when said male fluid connector portion and an associated female fluid connector portion are brought into engagement. The alignment guide may comprise a physical alignment feature that ensures connector alignment. For example, the alignment guide may comprise one or more protruding alignment prongs, or complimentary alignment slots and/or grooves etc. The alignment guide may also be provided by the relative positioning of the needles themselves. Alternatively, the alignment guide may comprise one or more visible markings to aid proper connector alignment. The alignment guide is thus arranged so that the hollow needles of the male fluid connector portion are uniquely aligned with the respective resilient membranes of the female fluid connector portion when the portions are connected together. This ensures that fluid communication is separately established between the required lumens of the tubing attached to the male and female fluid connector portions.

Conveniently, the male fluid connector portion comprises a substantially cylindrical portion having a screw thread for engaging the complementary screw thread of a female connector. Advantageously, the substantially cylindrical portion of the male fluid connector portion is rotatable relative to the remainder of the male fluid connector portion. The cylindrical portion may thus be a rotatable cylindrical portion having a screw thread formed on its inner surface such that, when the screw thread of the cylindrical portion engages the complementary screw thread of a female connector, rotation of the rotatable cylindrical portion acts to bring the male and female connectors into engagement. In this manner, the male and female fluid connector portions may be connected using a simple screw action.

Advantageously, the distal tip of each of said plurality of hollow needles is located within the volume enclosed by the cylindrical portion. In other words, the cylindrical portion encases the hollow needles thereby preventing inadvertent damage to such needles prior to, or during, connection.

Preferably, the longitudinal axes of each of said plurality of hollow needles are substantially parallel to the longitudinal axis of said cylindrical portion. If the male fluid connector portion comprises alignment guide means having one or more protruding alignment prongs, the longitudinal axis of each protruding alignment prong may also be substantially parallel to the longitudinal axis of said cylindrical portion. Furthermore, one of said one or more alignment prongs may conveniently be substantially co-axially aligned with said cylindrical portion.

Advantageously, the distal end of each alignment prong protrudes beyond the volume enclosed by the cylindrical portion. In other words, the distal end of the alignment prongs may be arranged to extend beyond the casing of the male fluid connector portion. Preferably, at least two alignment prongs are provided to allow the orientation of the male and female connector portions to be uniquely aligned. This arrangement permits the alignment prong(s) to enter the recesses of the corresponding female fluid connector portion, thereby angularly and axially aligning the male and female portions, before the hollow needles are brought into contact with the resilient membranes of the female connector portion. As described below, this prevents lateral forces being exerted on the hollow needles during the connection process.

The plurality of hollow needles and the alignment prongs are preferably arranged in a first pattern. For example, they may be evenly angularly displaced a certain radial distance from the longitudinal axis of the cylindrical portion. Any other configuration is possible as required. As outlined below, the female fluid connector portion is preferably arranged to have series of recesses and resilient membranes that adopt a pattern that is complimentary to said first pattern.

A wide variety of different material(s) may be used to form the hollow needles. The hollow needles may be formed from a combination of different material and may also comprise one or more coatings on the outer and/or inner surfaces as required. For example, the hollow needles may conveniently comprise at least one of silica, stainless steel, tungsten, tungsten carbide, titanium, titanium carbide, ceramic and plastic.

The hollow needles may conveniently each comprise a hollow core in which a fluid carrying tube (e.g. from an associated length of tubing) can be located. In a preferred embodiment described below, the hollow needles are formed from stainless steel and contain an inner silica core through which fluid can be passed. Silica is advantageous because it is not susceptible to the build up of foreign matter (e.g. bacteria).

The male fluid connector portion may comprise as many hollow needles as required. If a multi-lumen tube is terminated at said male fluid connector portion, the connector portion may comprise sufficient hollow needles to establish a separate fluidic link with each of said lumens. The male fluid connector portion may be arranged to retain a maximum number of needles, but when used it may be arranged to contain fewer needles than said maximum if required. The male fluid connector portion preferable comprises at least three hollow needles, at least four hollow needles, at least five hollow needles, at least six hollow needles, at least seven hollow needles, at least eight hollow needles, at least ten hollow needles, or at least fifteen hollow needles.

Advantageously, the male fluid connector portion is arranged to receive tubing comprising a plurality of lumens, wherein fluid communication is provided between each lumen and an associated one of said plurality of hollow needles. The male connector portion may also be attached (e.g. permanently) to a length of tubing having a plurality of lumens, each lumen being in fluid communication with one of said hollow needles. The tubing may, for example, comprise a sheath containing a plurality of tubes. In such a case, the sheath may be cut back and the proximal end of a hollow needle may be attached to each tube. The sheath may also be arranged to have a portion moulded or attached to its end which prevents the tubing being withdrawn from the connector. The sheath may also be toughened as required, although the tubing is preferably flexible.

Following the above, a female fluid connector portion may advantageously be provided which comprises a plurality of chambers, each chamber comprising a resilient membrane through which a hollow needle can be passed. Such a female connector portion may be connected to a male connector portion of the type described above. Each chamber of the female fluid connector portion may be in fluid communication with the lumen of an outlet tube and the resilient membrane is arranged to provide a resealable wall through which the hollow needle of a male connector can be passed thereby establishing fluid communication between the core of the hollow needle and the chamber. In a preferred embodiment, there is provided a female fluid connector portion for tubing having a plurality of lumens, the female fluid connector portion being releaseably connectable to a complimentary male fluid connector portion, the female fluid connector portion comprising; a plurality of chambers, each chamber comprising a septum seal through which a hollow needle can be passed, wherein, when tubing having a plurality of lumens is coupled to the female connector portion, each lumen is in fluid communication with one of said chambers; and an alignment guide that allows the septum seals to be uniquely aligned with the corresponding hollow needles of an associated complimentary male fluid connector portion.

The female fluid connector portion preferably comprises an alignment guide. The alignment guide or alignment guide means being arranged to provide alignment of said female fluid connector portion with a complimentary male fluid connector portion when said female and male fluid connector portions are brought into engagement. The alignment guide may be a physical feature; for example, the alignment guide of the female fluid connector portion comprises at least one elongate recess for receiving an alignment prong of an associated male fluid connector portion. The alignment guide may alternatively comprise at least one visible marking. Such guide means are described in more detail above in connection with the male connector portion. It should also be noted that the guide means of the male connector portion may comprise a recess or recesses for receiving the alignment prong(s) of a female connector; the definition of "male" and "female" connector portions is, herein, based only on the presence or absence of the hollow needles.

Advantageously, the female fluid connector portion comprises a second cylindrical portion having a screw thread for engaging the complementary screw thread of a male connector. If alignment guide means are provided that comprise at least one elongate recess for receiving an alignment prong of an associated male fluid connector portion, the longitudinal axis of said at least one elongate recess is preferably substantially parallel to the longitudinal axis of said second cylindrical portion. Conveniently, when the rotatable screw thread of a complimentary male fluid connector portion engages and is rotated relative to the screw thread portion of the female connector, hollow needles of the associated male connector portion are translated only in a direction that is substantially perpendicular to the plane of said resilient membranes.

In this manner, any substantial lateral movement of the hollow needles of the associated male fluid connector portion is prevented; this ensures such needles do not shear, snap or bend when the connection is made.

Conveniently, the female fluid connector portion comprises an outer casing having an annular end portion comprising a plurality of apertures through which the resilient membrane of each chamber can be accessed. Advantageously, the resilient membrane of each chamber is provided by a common annular, resilient, member retained against the inner surface of the annular end portion. Such a common annular, resilient, member may comprise one or more apertures aligned with the recess or recesses of the alignment guide means.

Advantageously, the female fluid connector portion is arranged to receive tubing comprising a plurality of lumens, wherein fluid communication is provided between each lumen and an associated one of said chambers. The number of lumens of the tubing may be equal to the number of chambers. The female fluid connector portion may also be attached to a length of tubing having a plurality of lumens, each lumen being in fluid communication with one of said chambers.

Preferably, the resilient membrane of each chamber comprises rubberised material. Advantageously, the resilient membrane is arranged to provide a fluidic seal that prevent egress of fluid through said membrane when no needle is inserted therethrough. In this manner a self sealing female connector portion is provided.

Accordingly, a connector may advantageously be provided which comprises a male fluid connector portion and a female fluid connector portion. In a preferred embodiment, there is provided a connector for tubing having a plurality of lumens, the connector comprising a male portion comprising a plurality of hollow needles and a female portion comprising a plurality of septum seals through which said plurality of hollow needles can be passed, wherein the connector comprises an alignment guide for uniquely aligning the hollow needles of the male portion with defined septum seals of the female fluid connector when the male fluid connector portion and the complementary female fluid connector portion are brought into engagement. The connector may be a medical connector; for example, it may be suitable for implantation as part of the modular fluid delivery apparatus described above.

Furthermore, a connector apparatus kit may be provided that comprises at least one of a male fluid connector portion and a female fluid connector portion of the type described above. The kit may further include at least one of a length of tubing, a catheter, a fluid pump and an implantable housing for encasing said connector part.

A first part of modular fluid delivery apparatus is described above that comprises a first length of tubing having a first fluid connector portion at its first end and being connected to one or more catheters at its second end. The first part of the modular fluid delivery apparatus may be implanted within the human or animal body.

To aid such implantation, surgical apparatus (also termed an "introducer") may be provided for introducing an elongate flexible member into the body, the apparatus comprising a first connector portion located at the distal end of an elongate deformable rod. Advantageously, said connector portion is releaseably attachable to a complimentary connector portion provided on an associated elongate flexible member. Introducer apparatus of this type may thus be used to implant within a human or animal body the first part of modular fluid delivery apparatus of the type described above or any other elongate flexible member (e.g. a length of electrical cable or tubing) which is terminated at a connector portion.

The apparatus is suitable for insertion into a first incision formed in the body and is sufficiently stiff so that it can be forced through the body so that it exits therefrom via a second incision. The elongate deformable rod is thus preferably radially bendable and axially stiff. In other word, the rod may take the form of a thick wire-like structure that can be deformed (bent) radially but is sufficiently stiff along its length so that it can be urged through the body. In this manner, the rod may be bent prior to, or during, entry to the body so that its distal end may be guided by a surgeon along a desired route through the body between a pair of incisions (e.g. at the scalp and chest). Advantageously, the elongate deformable rod comprises metal.

Unlike prior art introducer devices that comprise a sleeve through which tubing may be passed, the present apparatus permits an elongate flexible member (e.g. a cable and/or tubing) having a connector already attached thereto to be routed through the body. This allows the connector to be formed with, or attached to, the tubing prior to insertion within the body thereby negating the requirement to make multiple connections between tubing and the connector during the surgical procedure. The introducer is also substantially stiffer than hollow sleeve type arrangements thereby increasing the ease of passage through tissue.

Advantageously, a handle portion is provided at the proximal end of the elongate deformable rod. This provides increased control over the movement of the apparatus as it is passed through the body.

Preferably, the first connector portion is a fluid connector portion. For example, the connector portion of the apparatus may be arranged to connect to a complimentary male or female fluid connector portion of the type described above. The connector portion may also provide one or more electrical connections.

Conveniently, the introducer further comprises an end cap, the end cap comprising a complimentary connector portion releaseably attachable to the connector portion of the elongate deformable rod. The end cap preferably has a tapered outermost surface. For example, the end cap may be cone shaped, pointed or domed. The end cap may be attached to the connector portion at the distal end of the rod prior to insertion into the body. The outermost surface of the end cap will then form the necessary channel as the apparatus is forced through the body. The end cap may be removed one the distal end of the rod has exited the body via the second incision thereby allowing attachment of the connector portion of an elongate flexible member.

Advantageously, the apparatus further comprises an implantable elongate flexible member, the elongate flexible member comprising a connector portion that is attachable to the connector portion located at the distal end of the elongate deformable rod. The elongate flexible member preferably comprises tubing which may advantageously comprise a plurality of lumens. In other words, the tubing may comprise a number of internal cores for carrying fluid.

Accordingly, a method of introducing an elongate flexible member into the human or animal body is provided, the method comprising the steps of; (i) making a first incision and a second incision in said body, (ii) taking an elongate deformable rod having a first connector portion located at the distal end thereof, inserting the distal end of said elongate deformable rod into said first incision and guiding said elongate deformable rod through said body until the distal end exits the body through the second incision, and (iii) taking an elongate flexible member comprising a second connector portion, connecting the second connector portion to the first connector portion and withdrawing the elongate deformable rod from the body through said first incision.

Conveniently, step (i) comprises making a first incision in the torso and a second incision in the scalp. In this manner, the elongate flexible member may be tunnelled from the scalp to the torso via the neck. Advantageously, step (ii) comprises taking an elongate deformable rod having an end cap connected to the first connector portion, the end cap having a tapered outer surface. As described above, such an end cap ease the insertion of the rod into the body. The end cap may be removed prior to making the connection of step (iii).

Conveniently, step (ii) comprises subcutaneously guiding said elongate deformable rod through said body. In other words, the elongate flexible member may be tunnelled under the surface of the skin.

The invention will now be described, by way of example only, with reference to the accompanying drawings in which.

Figure 3:
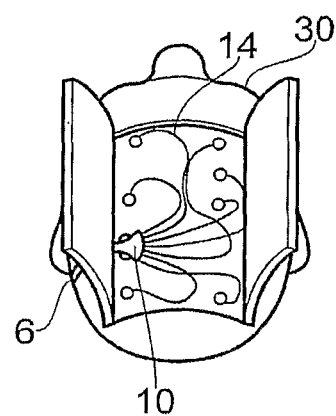
Figure 2:
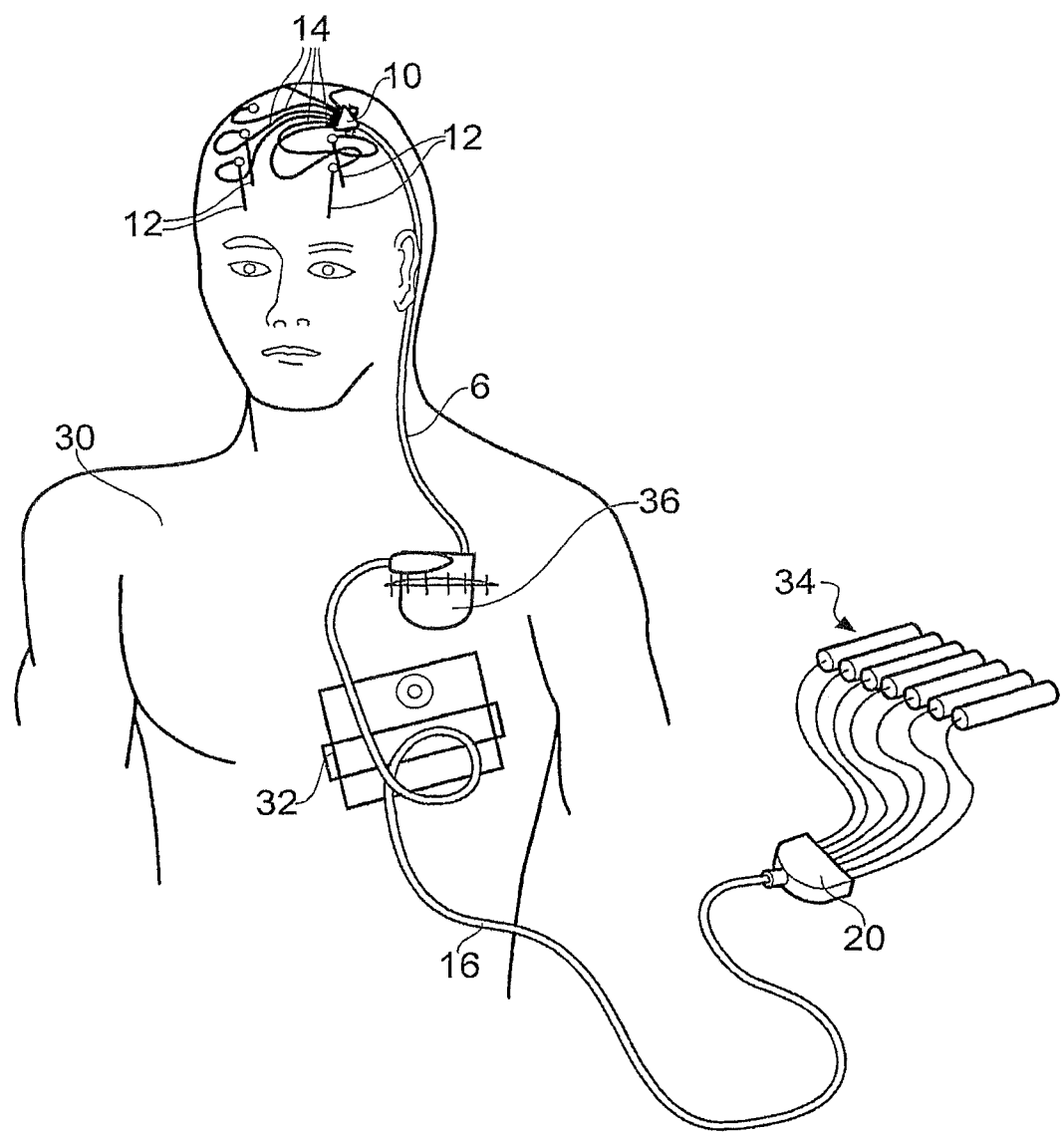
FIG. 2 illustrates the apparatus of FIG. 1 implanted in a subject.
Figure 4:
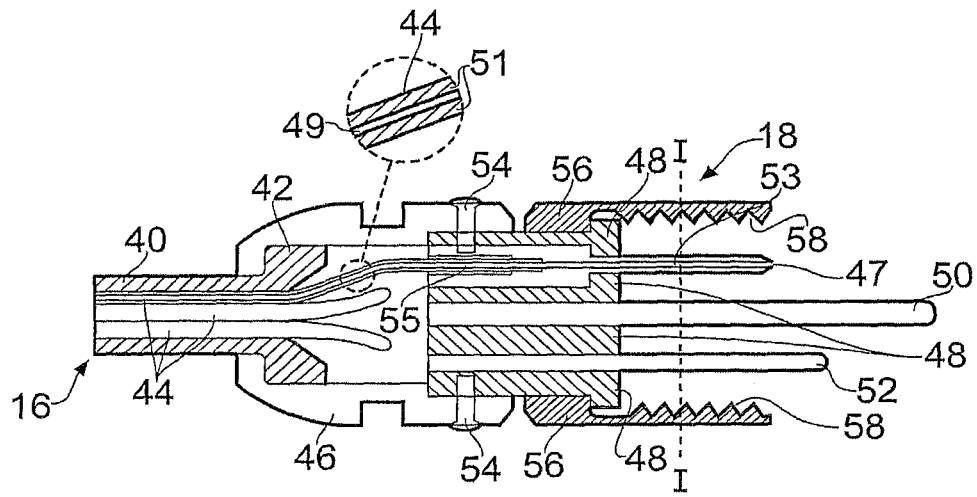
Figure 5:
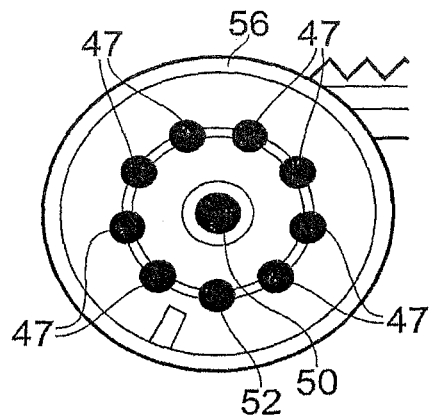
Figure 6:
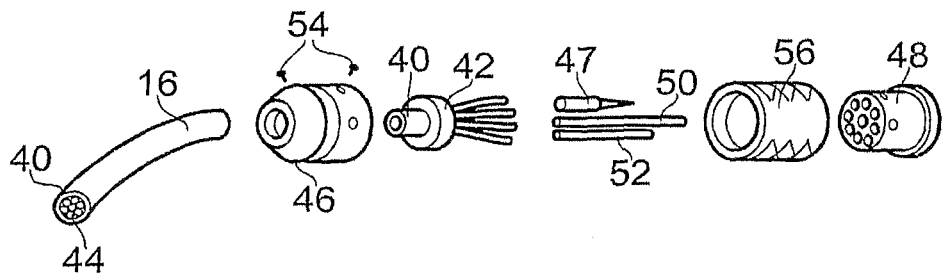
Figure 7:
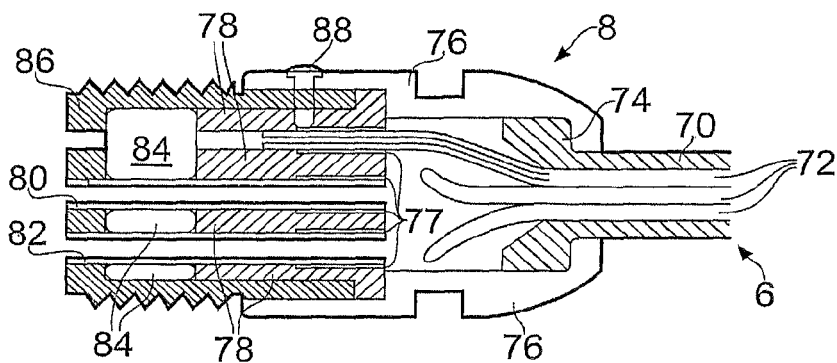
Figure 8:
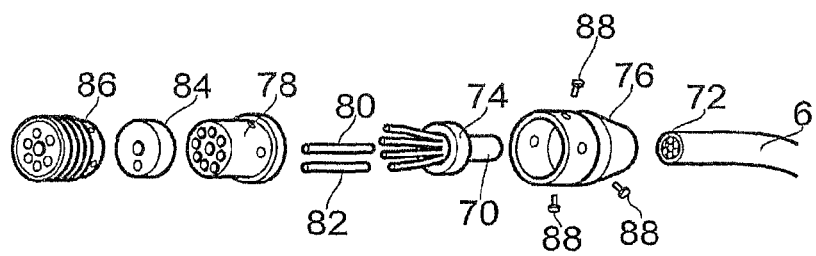
Figure 9:
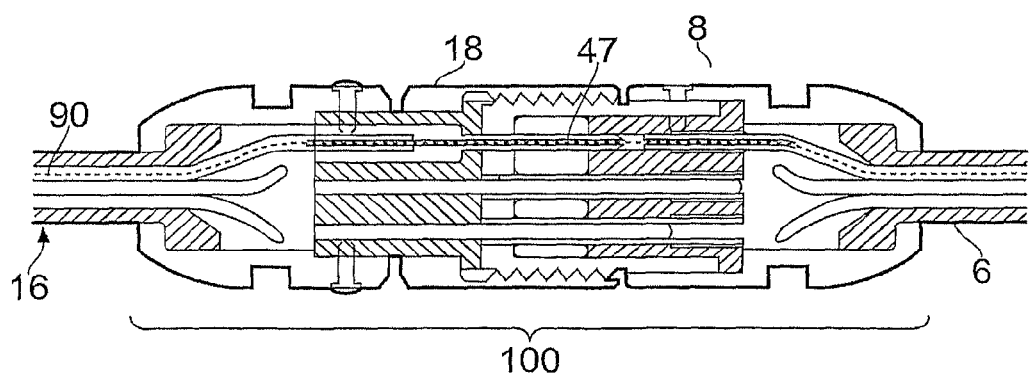
Figure 10:
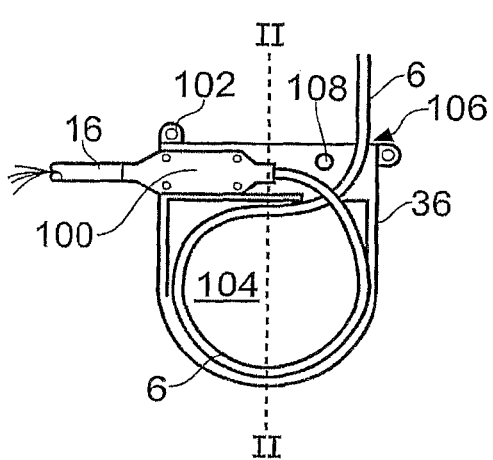
Figure 11:
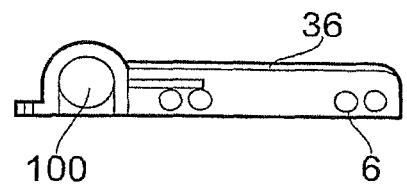
Figure 12:
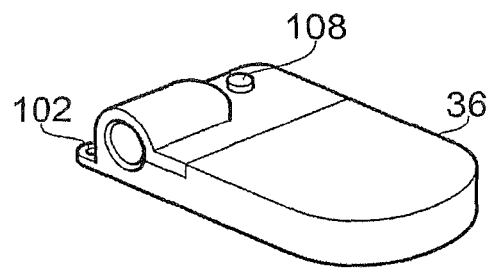
Figure 13:
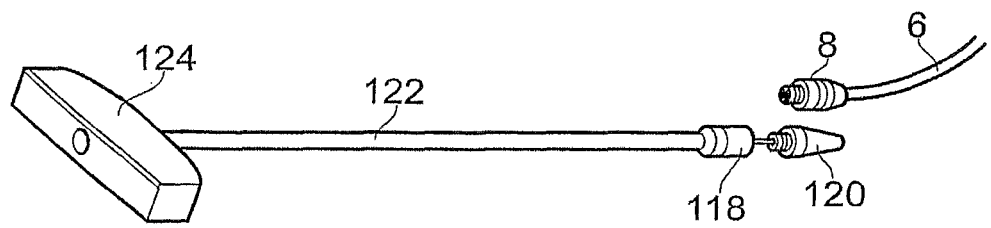

FIG. 3 gives an expanded view of the head of the subject of FIG. 2,

FIG. 4 is a sectional view along a male connector portion,

FIG. 5 is a cross-sectional view of the male connector portion of FIG. 4,

FIG. 6 is an exploded view of a connector portion of the type shown in FIGS. 4 and 5, FIG. 7 is a sectional view along a female connector portion, FIG. 8 is an exploded view of a connector portion of the type shown in FIG. 7, FIG. 9 illustrates the male connector portion of FIGS. 4 to 6 connected to the female connector portion of FIGS. 7 and 8, FIG. 10 shows a cut away plan view of an implantable housing for retaining a connector, FIG. 11 is a cross-sectional view of the housing of FIG. 10, FIG. 12 shows the external shape of the housing of FIGS. 10 and 11, FIG. 13 shows introducer apparatus, and FIG. 14 lists various drugs which could be delivered using the apparatus of FIGS. 1 to 12.

Figure 1:
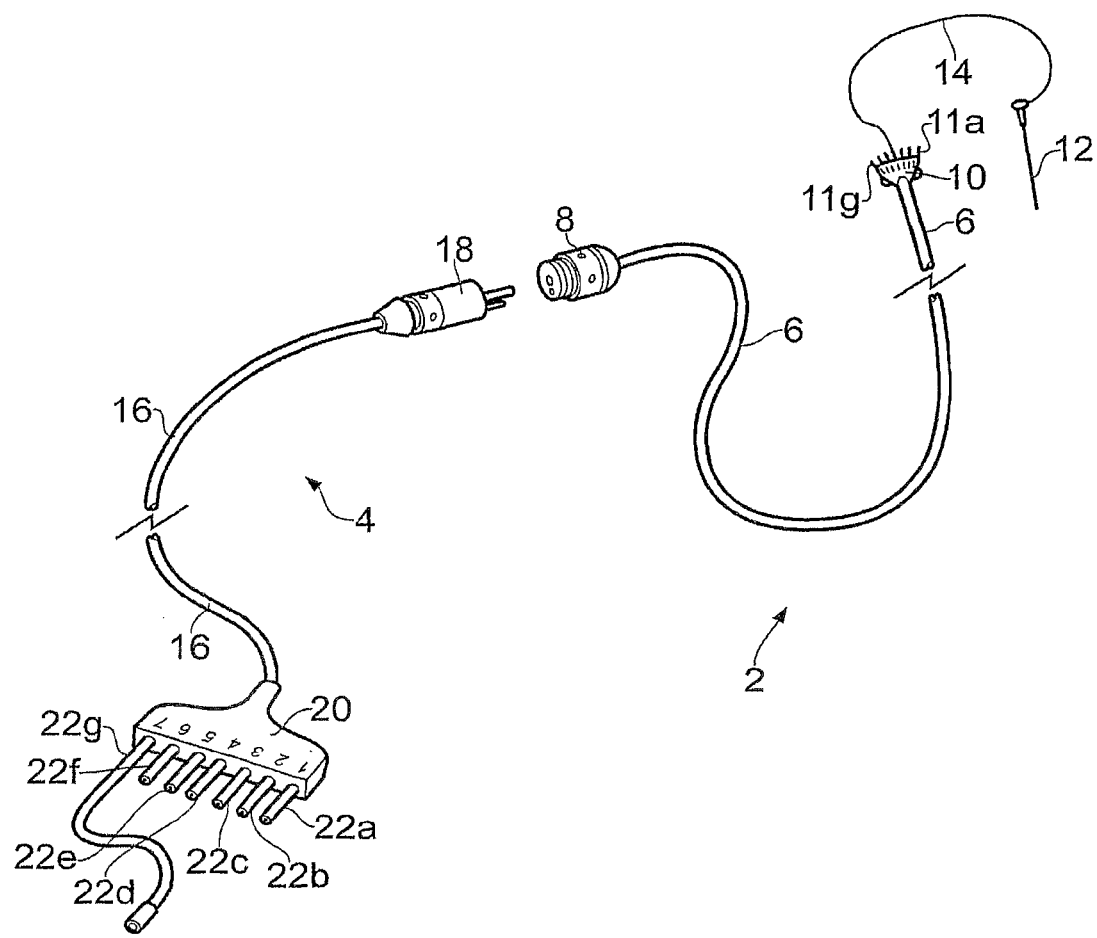
FIG. 1 illustrates modular drug delivery apparatus.

Referring to FIG. 1, apparatus for delivering a drug to the brain of a subject is shown. The apparatus is modular and comprises a first part 2 and a second part 4.

The first part 2 of the apparatus comprises a first seven-lumen tube 6 that couples a female seven-lumen connector portion 8 to an implantable fluidic router 10. The fluidic router 10 has seven outputs 11a-11g. Each of the outputs 11 is connected to an associated catheter 12 via a length of single lumen tubing 14 (noting that only one such catheter is shown in FIG. 1). The second part of the apparatus comprises a second seven-lumen tube 16 that couples a male seven-lumen connector portion 18 to an external fluidic router 20. The external fluidic router 20 has seven inputs 22a-22g, each input being suitable for receiving fluid under pressure from an associated pump assembly.

The male seven-lumen connector portion 18 of the second part is arranged to mate with the female seven-lumen connector portion 8 of the first part so that fluid communication can be established between respective lumens of the first seven-lumen tube 6 and the second seven-lumen tube 16. In this manner, fluid communication is separately established between each of the seven router inputs 22 and an associated catheter 12.

Referring to FIGS. 2 and 3, the apparatus of FIG. 1 is illustrated when arranged to deliver a drug to the brain of a subject 30. In particular FIG. 2 shows the upper body of a subject and FIG. 3 gives an expanded view of the top of the head of that subject.

The first part 2 of the apparatus is fully implanted within the subject 30 and will typically remain in situ for the duration of a course of treatment (which may include multiple periods of drug delivery). Implantation of the first part 2 of the apparatus will necessarily involve a complex surgical procedure in which the tips of the interparenchymal catheters 12 are carefully positioned at the required locations within the brain. This procedure will also require implantation of the various lengths of single lumen tubing 14, the mounting of the implantable fluidic router 10 to the skull and sub-cutaneous tunnelling of the first multi-lumen tube 6 from the scalp to the chest region.

A detailed view of the implantable fluidic router 10, the single lumen tubing 14 and the proximal ends of the catheters 12 after surgical implantation in the head of the subject is given in FIG. 3. The arrangement of the seven catheters shown in FIG. 3 allows delivery of a drug to the entire brain Two catheters ($F_1$ and $F_2$) are inserted to deliver drug to the left and right frontal lobes. A further pair of catheters ($P_1$ and $P_2$) are inserted to permit delivery to the left and right parieto-occipital lobes. Two more catheters ($T_1$ and $T_2$) are inserted so as to delivery drugs to the left and right tempo-occipital lobes and a catheter ($P_s$) is inserted into the pons to allow drugs to be driven down into the cerebellum through the white matter tracks.

The male seven-lumen connector portion 18 of the second part 4 of the apparatus is connected to the female seven-lumen connector portion 8 of the first part 2 of the apparatus. The connector is retained in a housing 36 that may be anchored to the subject (e.g. by a suture). The second length of seven-lumen tubing is passed through an incision 32 in the thorax (e.g. in the chest) and each input 22 of the external fluidic router 20 is connected to a fluidic output of an external pump assembly 34. As the tubing 16 enters the body at an anatomical location which is a significant distance from the central nervous system (CNS), the possibility of any infection at the aperture reaching the CNS is minimised.

Once implanted, the apparatus provides a separate fluidic pathway from each of the seven outputs of the pump assembly 4 to an associated one of the seven catheters 18. This allows fluid to be routed to any one of the seven catheters as required.

The drug delivery profile (e.g. drug concentration, fluidic pressure, flow rate etc) may thus be set as required by a clinician by suitably programming the external pump assembly 34. The pump assembly 34 may be arranged to pump fluid to the catheters in any desired manner; for example, drug may be delivered sequentially or simultaneously to the different catheters.

As shown in FIG. 2, the pump assembly comprises seven different outputs, each of which is connected to one of the router inputs 22. The provision of such an external pump assembly allows the administration of drugs that have short half lives and/or which must be stored at low temperatures and/or which must be delivered in large volumes. External pumps also have the advantage of being readily accessibly (compared with implanted pumps) in case of failure or malfunction.

The modular apparatus described herein allows the second part 4 of the apparatus to be disconnected from the first part 2 of the apparatus when drug delivery is no longer required. The removal of the second part 4 involves a relatively simple surgical procedure in which the chest incision is re-opened and the first and second parts of the apparatus are disconnected. Subsequently, when an additional dosage of drug is to be delivered, the second part 4 can be reconnected to the first part 2 by reversing such a procedure.

The apparatus thus allows an initial, rather complex, surgical procedure to be performed in which the first and second parts of the apparatus is implanted as described above. A first dose of the necessary drugs can then be given, after which a relatively simple surgical procedure can be performed to remove the second part of the apparatus from the subject. After the second part of the apparatus is removed, the subject may be temporarily discharged from medical care and, because the remaining first part of the apparatus is fully implanted within the body, there will be no tubes exiting the body that need to be kept sterile to prevent infection. After a suitable period of time, the subject may undergo a further, again relatively simple, surgical procedure that involves making an incision in the chest and reconnecting a second part of the apparatus to the first part of the apparatus. This may be followed by the administration of a further dose of the required drug(s) and subsequent surgical removal of the second part of the apparatus. This may be repeated as many times, and as frequently, as required. If the treatment is completely successful, the first part of the apparatus may also be removed from the subject.

Referring to FIGS. 4 to 6, the structure of the male seven-lumen connector portion 18 and the associated seven-lumen tubing 16 will now be described.

The tubing 16 received by the connector portion 18 comprises an outer cable sheath 40 within which a bundle of seven single lumen tubes 44 are retained. The cable sheath also comprises a radially extending end portion 42. The male connector portion 18 comprises an end cap portion 46 having an aperture through which the tubing 16 is passed. The radially extending end portion 42 of the cable sheath 40 is arranged to prevent the cable being drawn back though the aperture of the end cap portion 46. The seven single lumen tubes 44 fan out within the end cap portion 46 and are each routed to a hollow needle 47. It should be noted that, for clarity, only a single needle is illustrated in FIGS. 4 and 6.

Each hollow needle 47 is formed of a resilient, preferably rigid, material. The hollow needles 47 may thus be formed from a metal or any suitable material; for example, the hollow needles may comprise stainless steel, tungsten, tungsten carbide, titanium, titanium carbide, plastic etc. As shown in the inset of FIG. 4, each of the single lumen tubes 44 comprises an inner fused silica tube 49 (i.e. defining the lumen) that is surrounded by protective plastic cladding 51. To connect the single lumen tube 44 to the needle 47, the cladding 51 is removed from a region at the distal end of each tube 44. Each needle 47 is arranged such that the inner fused silica tube (absent any cladding) can pass through the hollow core 53 that runs to the distal end (or tip) of the needle and also comprises, at its proximal end, an aperture 55 for receiving the silica tube 49 with cladding 51 attached thereto. The tubing 44 (with the cladding stripped back from its end) can thus be inserted into the needle until the cladding fills the aperture 55; the exposed length of silica core at the end of the tube 44 can also be made sufficiently long to extend the tip of the hollow needle. Once inserted, the tubing may be bonded to the needle 47 using adhesive or any other suitable attachment means. In this manner a fluidic seal can be readily established.

The male connector portion also comprises a retaining block 48 having a central aperture and eight further radial apertures that are angularly spaced about the central aperture. A first alignment prong 50 is retained within the central aperture of the retaining block 48 and a second alignment prong 52 is retained within one of the radial apertures of the retaining block 48. The seven needles 47 are retained in the remaining radial apertures of the retaining block 48. The needles 47 and alignment prongs 50 and 52 may be secured to the retaining block 48 by any appropriate means (e.g. by adhesive, welding, bonding or with appropriate fixings etc). Screws 54 are also provided to fix the end cap portion 46 to the retaining block 48.

A cylindrical casing portion 56 is also provided which is rotatably mounted to the retaining block 48. The cylindrical casing portion 56 has an internal screw thread 58 that mates with a complimentary screw thread of the female connector portion. The connector portion 18 is arranged such that the seven protruding needles 47 and the two alignment prongs 50 and 52 extend in directions that are substantially parallel to the central axis of the cylindrical casing portion 56. The needles 47 are arranged to extend no further than the end of the cylindrical casing portion 56, thereby reducing the possibility of the needles being accidentally broken or damaged. The first and second alignment prongs 50 and 52 are arranged to extend beyond the cylindrical casing 56 and the first (central) alignment prong 50 is arranged to extend further from the connector portion than the second alignment prong. The radial arrangement of the first and second alignment prongs and the associated needles are shown in detail in FIG. 5 which is a sectional view along the line I-I of FIG. 4.

Referring to FIGS. 7 and 8, the structure of a female seven-lumen connector portion 8 which is complimentary to the above described male connector portion 18 is shown.

The tubing 6 received by the female connector portion 8 comprises an outer cable sheath 70 within which a bundle of seven single lumen tubes 72 are retained. The cable sheath also comprises a radially extending end portion 74.

The female connector portion 8 comprises an end cap 76 having an aperture through which the tubing 6 is passed. The radially extending end portion 74 of the cable sheath 70 is arranged to prevent the cable being withdrawn though the aperture of the end cap 76. The seven single lumen tubes 72 are arranged to fan out within the end cap portion 76.

A cavity block 78 is also provided having a central aperture and eight further radial apertures that are angularly spaced about the central aperture. The relative positions of the nine apertures of the cavity block 78 are matched to the positions of the apertures of the retaining block 48 of the complimentary male connector portion 18. A first tubular portion 80 and a second tubular portion 82 are located within the central aperture of the cavity block and a radial aperture of the cavity block 78 respectively. The other seven radial apertures each receive an end of an single lumen tube 72. The ends of the single lumen tubes 72 and the first and second tubular portions 80 and 82 are retained within the apertures of the cavity block 78 by an appropriate fixing means 77 (e.g. using adhesive, welding, bonding or with appropriate fixings etc). The fixing means 77 also provides a fluidic seal between the single lumen tube 72 and the associated aperture of the cavity block.

Screws 88 are passed through the end cap portion 76 and a threaded end portion 86 in to the cavity block 78 thereby retaining such components in a fixed spaced relation. A annular rubber bung 84 is also retained within the threaded end portion 86 and is forced into engagement with the end of the cavity block 78. The rubber bung 84 has two apertures which are aligned such that the first and second tubular portions 80 and 82 pass therethrough. The threaded end portion 86 has an arrangement of apertures that match that of the cavity block 78 and an outer thread suitable for engaging the thread of the male connector portion 18.

The assembled female connector portion 8 thus comprises seven sealed apertures (i.e. sealed by the rubber bung 84) for receiving a needle and two apertures for receiving the alignment prongs of a complimentary male connector portion. The apertures for receiving the alignment prongs are arranged to have a larger diameter than the sealed apertures. A needle inserted into one of sealed apertures will pass through the rubber bung 84 and enter the associated cavity of the cavity block. In this manner, fluid communication can be established between the needle and the associated single lumen tube retained by that cavity. In the absence of such a needle, the apertures are sealed by the rubber bung 84 thus preventing fluid passage into, or out of, the associated tubes.

Referring to FIG. 9, a male connector portion 18 of the type described with reference to FIGS. 4 to 6 is shown when mated with a female connector portion 8 of the type described with reference to FIGS. 7 and 8 thus forming a connector 100.

Once the female connector portion 8 is mated with the male connector portion 18, seven separate fluidic connections are established between the seven lumens of the first and second seven-lumen tubes 6 and 16. The dashed line 90 of FIG. 9 illustrates the flow path from one lumen of the second seven-lumen tube 16, through the hollow needle 47 and into an associated lumen of the first seven-lumen tube 6.

A male connector portion 18 may be connected to a female connector portion 8 in the following manner. Firstly, the central alignment prong 50 of the male connector portion is located in the central first tubular portion 80 of the female connected. The male connector portion is then rotated relative to the female connector portion until the second alignment prong 52 enters the second tubular portion 82. At this point, the cylindrical casing 56 of the male connector portion 18 is rotated such that its internal screw thread 58 engages the complimentary thread of the threaded end portion 86 of the female connector portion 8. Further rotation of the cylindrical casing 56 of the male connector portion 18 urges the needles 47 through the rubber bung 84 and into the cavity of the cavity block. It should be noted that once the alignment prongs are aligned with the tubular portions, tightening the screw thread causes the needles to move in a direction that is substantially parallel to the longitudinal axes of the male and female connector portions. In other words, the needles are forced through the rubber bung from a direction substantially perpendicular to that bung; i.e. without any significant lateral movement which might cause such needles to deform or snap.

Unscrewing the cylindrical casing 56 from the threaded end portion 86 of the female connector portion 8 causes retraction of the needles 47 through the rubber bung, again without any substantial later movement. Once disconnected, the rubber bung 84 again acts to seal each cavity of the cavity block 78 thereby preventing egress of fluid from the first seven-lumen tube 6.

Referring now to FIGS. 10 to 12, a housing 36 of the type described above with reference to FIG. 2 is shown. In particular, FIG. 10 shows a plan view through the housing 36 with a connector 100 retained therein whilst FIG. 11 gives a cross-sectional view along the line II-II of FIG. 10. FIG. 12 provides a further view of the housing, absent a retained connector.

The housing 36 is designed to retain and enclose a connector 100 of the type described above. The connector provides fluidic connection between the lumens of the first seven lumen tube 6 and the second seven lumen tube 16. The housing also comprises attachment flanges 102 for securing the housing 36 to the human or animal body in which it is implanted using, for example, sutures.

In order to allow for movement of the subject after implantation of the drug delivery apparatus, the housing also comprises an internal cavity 104 in which a loose coil of a length of the first tubing 6 is located. The tubing 6 is arranged to exit the housing 36 via an aperture 106. Providing such a coil enables the subject to move freely; the coil of tubing extending and retracting as required with such movement. To allow easy connection and disconnection of the first and second parts of the drug delivery apparatus, the housing may comprise a flip top that is secured to the base with a screw 108. Undoing the screw 108 allow access to the internal cavity of the housing and hence to the connector 100.

Referring now to FIG. 13, surgical introducer apparatus is shown for subcutaneously tunnelling the first seven-lumen tube 6 from the scalp to the chest region. The introducer apparatus comprises a length of deformable flexible material 122 having a handle 124 at its proximal end and a pseudo-male connector portion 118 attached to its distal end.

The pseudo-male connector portion 118 is analogous to the male connector portion 18 described with reference to FIGS. 4-6 above, except that it does not include the needles 47 and is not connected to the seven-lumen tube 16. The pseudo-male connector portion 118 thus includes the rotatable cylindrical portion and the alignment prongs which allows it to be physically attached to a female connector portion 8 of the type described with reference to FIGS. 7 and 8. However, attaching the female connector portion 8 to the pseudo-male connector portion 118 does not break the fluidic seal provided by the rubber bung of the female connector portion 8.

A pseudo-female connector portion 120 may also be provided. The pseudo-female connector portion 120 has a screw thread that will engage the pseudo-male connector portion 118 an apertures for receiving the alignment prongs of the pseudo-male connector portion 118. The distal end of the pseudo-male connector portion 118 is cone shaped.

The introducer apparatus is used in the following manner. Firstly, incisions are made in the scalp of the subject allowing the catheters 12 and the implantable fluidic router 10 etc to be implanted as required. An incision is then made in the chest of the subject. The pseudo-female connector portion 120 is attached to the pseudo-male connector portion 118 of the introducer apparatus. The introducer is then inserted in the chest incision and pushed upwardly towards the scalp incision. Once the distal end of the introducer apparatus exits the subject via the scalp incision, the pseudo-female connector portion 120 is detached from the pseudo-male connector portion 118. The female connector portion 8 of the first part 2 of the drug delivery apparatus is then connected to the pseudo-male connector portion 118 and the introducer apparatus is withdrawn back through the chest incision. This withdrawal pulls the female connector portion 8 and the attached first seven lumen tubing 6 from the scalp to the chest. The pseudo-male connector portion 118 can then be disconnected from the female connector portion 8 and the male and female connectors may be connected to form a connector 100 which can be located in a housing 36.

Once implanted, the modular apparatus described above can be used for a wide variety of different treatments. Referring to FIG. 14, a number of potential applications for convection enhanced delivery to the brain are provided. In particular, the type of agent and the number of 0.2 mm outer diameter catheters required to deliver such an agent are shown. In certain circumstances, the delivery regimen may require continuous delivery whilst other treatments may require pulsed (bolus) delivery. It should be noted that the list of FIG. 14 is by no means exhaustive. The skilled person would appreciate the numerous applications in which apparatus of the type described above could be used.

The above apparatus specifically describes the delivery of drugs to the brain via seven catheters. It should be again noted that neither of these features are essential elements of the invention. Despite being particularly suited to delivering drugs to the central nervous system, the apparatus described above could be used to deliver any type of fluid to any part of the human or animal body. Furthermore, the apparatus could comprise any number of fluidic pathways from an external pump to internally implanted catheters.

The invention claimed is:

1. A method for delivering fluid to a brain of a subject who has a first part of using a modular fluid delivery apparatus subcutaneously implanted therein, the first part comprising a first length of tubing that has (i) a first end having a first fluid connector portion attached thereto and (ii) a second end connected to one or more catheters implanted within the brain of the subject, the method comprising the steps of:
    making an incision in the subject to gain access to the first fluid connector portion of the first part of the modular fluid delivery apparatus; and
    after the incision has been made in the subject, passing a second fluid connector portion of a second part of the modular fluid delivery apparatus through the incision and connecting the first fluid connector portion to the second fluid connector portion, the second part comprising a second length of tubing having an end that comprises the second fluid connector portion.

2. The method according to claim 1, further comprising the subsequent step of pumping fluid into the brain of the subject through the first and second parts of the modular fluid delivery apparatus and the one or more implanted catheters.

3. The method according to claim 2, further comprising the subsequent step of disconnecting the first fluid connector portion from the second fluid connector portion and completely withdrawing the second part of the modular fluid delivery apparatus from the subject.

4. The method according to claim 3, further comprising the subsequent step of closing the incision in the subject, thereby leaving the first part of the modular fluid delivery apparatus subcutaneously implanted in the subject.

5. The method according to claim 2, wherein the fluid pumped into the brain of the subject during the pumping step comprises a cytotoxic drug.

6. The method according to claim 2, wherein the fluid pumped into the brain of the subject during the pumping step comprises a neurotrophin.

7. The method according to claim 2, wherein the fluid pumped into the brain of the subject during the pumping step comprises a monoclonal antibody.

8. The method according to claim 2, wherein the fluid pumped into the brain of the subject during the pumping step comprises a viral particle.

9. The method according to claim 1, further comprising an initial step of implanting the first part of the modular fluid delivery apparatus in the subject.

10. The method according to claim 9, wherein the step of implanting the first part of the modular fluid delivery apparatus in the subject includes implanting the one or more catheters in the brain of the subject.

11. The method according to claim 1, wherein the first fluid connector portion implanted in the subject comprises a sealing member configured to prevent fluid egress when the first fluid connector portion is unconnected to the second fluid connector portion.

12. The method according to claim 11, wherein the sealing member comprises a septum seal.

13. The method according to claim 1, wherein the first length of tubing implanted in the subject has a single lumen.

14. The method according to claim 1, further comprising initial steps of:
    making one or more incisions in the subject;
    implanting the one or more catheters in the brain of the subject;
    subcutaneously implanting the first part of the modular fluid delivery apparatus in the subject; and
    closing the one or more incisions such that the first part of the modular fluid delivery apparatus and the one or more catheters are entirely subcutaneously implanted within the subject.

15. The method according to claim 14, wherein prior to the step of closing the one or more incisions, the method further comprises the steps of:
    connecting the first fluid connector portion to the second fluid connector portion; and
    pumping fluid to the one or more implanted catheters through the first and second parts of the modular fluid delivery apparatus.

16. The method according to claim 14, wherein the step of making the incision in the subject to gain access to the first fluid connector portion occurs after the step of closing the one or more incisions.

17. The method according to claim 16, further comprising the subsequent step of:
    pumping fluid to the one or more implanted catheters through the first and second parts of the modular fluid delivery apparatus.

18. The method according to claim 17, further comprising the subsequent steps of:
    disconnecting the first fluid connector portion from the second fluid connector portion; and
    completely withdrawing the second part of the modular fluid delivery apparatus from the subject.

19. A method for delivering fluid to a brain of a subject, the method comprising the steps of:
    making one or more incisions in a subject;
    implanting one or more catheters in the brain of the subject;
    subcutaneously implanting a first part of a modular fluid delivery apparatus in the subject, the first part of the modular fluid delivery apparatus comprising a first length of tubing having a first end and a second end, the first end having a first fluid connector portion attached thereto and the second end being connected to the one or more catheters;
    making a subsequent incision in the subject to gain access to the first fluid connector portion of the first part of the modular fluid delivery apparatus;
    after the subsequent incision has been made in the subject, passing a second fluid connector portion of a second part of the modular fluid delivery apparatus through the subsequent incision and connecting the first fluid connector portion to the second fluid connector portion, the second part comprising a second length of tubing having an end that comprises the second fluid connector portion; and
    pumping fluid into the brain of the subject through the modular fluid delivery apparatus and the one or more catheters.

20. A method for delivering fluid to a brain of a subject who has a first part of a modular fluid delivery apparatus subcutaneously implanted therein, the first part comprising a first length of tubing that has (i) a first end having a first fluid connector portion attached thereto and (ii) a second end connected to one or more catheters implanted within the brain of the subject, the method comprising the steps of:
    making an incision in the subject through which a second length of tubing of a second part of the modular fluid delivery apparatus can be passed, the incision uncovering and thereby providing access to the first fluid connector portion of the first part of the modular fluid delivery apparatus; and
    subsequently connecting, through the incision, the first fluid connector portion to a second fluid connector portion at an end of the second length of tubing of the second part of the modular fluid delivery apparatus.

\* \* \* \* \*